United States Patent [19]

Ueda et al.

[11] Patent Number: 5,405,628
[45] Date of Patent: Apr. 11, 1995

[54] FEED ADDITIVE COMPOSITION FOR RUMINANTS

[75] Inventors: Satoshi Ueda; Haruo Heima; Makoto Ozawa; Takeshi Nagai; Tsuyoshi Nakamatsu; Hiroyuki Sato, all of Kawasaki, Japan

[73] Assignee: Ajinomoto Co., Inc., Tokyo, Japan

[21] Appl. No.: 122,656

[22] Filed: Sep. 17, 1993

[30] Foreign Application Priority Data

Sep. 17, 1992 [JP] Japan ................... 4-248196
Aug. 9, 1993 [JP] Japan ................... 5-197052

[51] Int. Cl.$^6$ ............................................. A23K 1/18
[52] U.S. Cl. .................................. 426/99; 424/438; 426/72; 426/74; 426/656; 426/807
[58] Field of Search ............ 426/99, 807, 72, 74, 426/656; 424/438, 442, 476

[56] References Cited

U.S. PATENT DOCUMENTS

| | | | |
|---|---|---|---|
| 2,560,830 | 7/1951 | Turner | 426/99 |
| 2,683,664 | 7/1954 | Greer | 426/99 |
| 3,468,667 | 9/1969 | Chandler | 426/99 |
| 3,686,392 | 8/1972 | Hamada | 424/442 |
| 5,227,166 | 7/1993 | Ueda et al. | |
| 5,229,147 | 7/1993 | Kubota | 426/807 |

OTHER PUBLICATIONS

Patent Abstracts of Japan, vol. 15, No. 189 (C-0831), JP-A-3047523, Feb. 28, 1991.
Patent Abstracts of Japan, vol. 13, No. 158 (C-586), JP-A-63317053, Dec. 26, 1988.
Patent Abstracts of Japan, vol. 16, No. 54 (C-0909), and JP-A-3254643, Nov. 13, 1991.
Journal of Dairy Science, vol. 40, No. 12, pp. 1617–1620, J. M. Wing, "Effect Of Method Of Feeding Menthionine And Potassium Orotate To Young Calves", 1957.

Primary Examiner—Geoffrey L. Knable
Assistant Examiner—Daniel J. Stemmer
Attorney, Agent, or Firm—Oblon, Spivak, McClelland, Maier, & Neustadt

[57] ABSTRACT

A feed additive composition is provided having a core which contains a biologically active substance and which is coated with a coating composition which contains components a) and b):

a) at least one substance selected from the group consisting of linear or branched saturated or unsaturated aliphatic monocarboxylic acids of 12–22 carbon atoms or salts thereof, hardened vegetable fats and oils, hardened animal fats and oils, and wax; and b) at least one of substances i) and ii):
  i) one or more linear or branched saturated or unsaturated aliphatic monocarboxylic acids of 11 carbon atoms or less, and
  ii) one or more substances selected from the group consisting of nucleic acids, nucleotides, nucleosides, bases composing nucleic acids and salts thereof.

14 Claims, No Drawings

FEED ADDITIVE COMPOSITION FOR RUMINANTS

BACKGROUND OF THE INVENTION

1. Field of the Invention:

The present invention relates to a feed additive composition. More specifically, it relates to a feed additive composition for ruminant animals wherein a biologically active substance is coated with a coating composition which is stable in the animal's rumen but which allows the release of the biologically active substance in the abomasum and subsequent digestive tract, thus making possible the digestion of the biologically active substance without significant loss due to rumen microbe degradation.

2. Description of the Related Art

When biologically active substances such as amino acids, vitamins, etc. are orally administered to ruminants like cattle and sheep, the majority of the active substance is decomposed by microorganisms which are present in the rumen, and the substance is not utilized effectively by the animal. Accordingly, biologically active substances which are capable of passing through the rumen without decomposition and which are then effectively digested and absorbed in the abomasum and subsequent digestive tract are desired in the field of ruminant feeds, nutrient preparations, medicines, etc.

Feed additives for ruminants containing biologically active substances have been proposed in the past. These materials are coated with fatty acids with 12 or more carbon atoms, hardened animal or vegetable fats and oils, etc. Unfortunately, however, these particles coated with fats and oils are stable not only in the rumen, but also in the abomasum and subsequent digestive tract, making release and digestion of the biologically active substances poor. For this reason, methods of adding to the protective substances substances which enhance release in the abomasum and subsequent digestive tract have been proposed. In these methods, the biologically active materials are dispersed in coating materials and granulated, or are coated with the coating materials.

A method for the dispersion of a biologically active substance in a protective substance has been proposed in, for example, Japanese Unexamined Patent Application 168351/85A, wherein granules are produced containing a biologically active substance, 20% by weight or more of calcium carbonate, 10% by weight or more of an aliphatic monocarboxylic acid of 14 or more carbon atoms, a hardened fat or oil, etc. Also, In Japanese Examined Patent Application 10780/84B a method is proposed for dispersing 30–50% by weight of a biologically active substance into a protective substance comprising 10–35% by weight of salt of aliphatic monocarboxylic acid of 14–22 carbon atoms or ricinoleic acid, the remainder comprising an aliphatic monocarboxylic acid of 14–22 carbon atoms, ricinoleic acid, hardened fats and oils, or the like.

A method for coating a biologically active substance with a protective substance has also been proposed in Japanese Unexamined Patent Application 317053/88A, wherein a biologically active substance is coated with a protective substance which comprises an aliphatic monocarboxylic acid of 12–24 carbon atoms, a hardened fat and oil, lecithin, and a glycerin fatty acid ester.

However, in these methods for preparing dispersions of biologically active substances in protective substances, since the biologically active substance is present near the particle surface, it is necessary to significantly lower the content of the biologically active substance for its protection, and, considering that, in the case of water-soluble biologically active substances, since the residence time in the rumen is from a few dozen hours to a few days, sufficient protection thereof is difficult to provide. In addition, when coating is accomplished using a protective coating consisting of lecithin, a glycerin fatty acid ester, and a fat and an oil, the strength of the coating layer in the rumen is insufficient and the problem of poor protection remains. Furthermore, the lecithin and glycerin fatty acid esters are expected to have an emulsifying effect on the fat and oil, but considering the time of passage through the abomasum and subsequent digestive tract, the degree of release is insufficient.

Finally, a method has been proposed for providing a coating using a synthetic polymer which is insoluble in the environment of the rumen, but which is soluble in the strongly acidic abomasum, in order to make use of the difference in pH of the rumen and the abomasum. However, considering the fact that this method uses an organic solvent during coating it leads to high costs, as well as to other negative factors, and thus cannot be said to be a fully adequate method.

SUMMARY OF THE INVENTION

In view of the prior art drawbacks, an object of the present invention is to stably protect biologically active substances in the rumen of ruminants while allowing efficient digestion and absorption of the substances in the abomasum and subsequent digestive tract, giving due consideration to safety and economy. Other objects will become obvious to the reader upon a full appreciation of the invention as described below, and as described in the claims.

DETAILED DESCRIPTION OF THE PREFERRED EMBODIMENTS

The present inventors have now discovered that it is possible to combine both excellent stability in the rumen and excellent release in the abomasum and subsequent digestive tract by coating a core which contains a biologically active substance with a coating composition which contains one or more linear or branched saturated or mono- or poly-unsaturated aliphatic monocarboxylic acids having 11 carbon atoms or less, (hereunder abbreviated to "lower fatty acids") and/or one or more substances selected from the group consisting of nucleic acids, nucleotides, nucleosides, bases composing nucleic acids and salts thereof (hereunder abbreviated to "nucleic acid-related substances"), as well as a substance selected from the group consisting of linear or branched saturated or mono- or poly-unsaturated aliphatic monocarboxylic acids of 12–22 carbon atoms and salts thereof, hardened vegetable fats and oils, hardened animal fats and oils, and wax. This discovery has lead to the completion of the present invention.

The present invention is directed to a feed additive composition, particularly one for ruminants, characterized in that a core which contains a biologically active substance is coated with a coating composition which contains at least a) and b) below:

a) at least one substance selected from the group consisting of linear or branched, saturated or mono- or polyunsaturated aliphatic monocarboxylic acids having 12–22 carbon atoms or salts thereof, hardened vegetable fats and oils, hardened animal fats and oils, and wax; and b) a substance indicated in i) and/or ii) below,
   i) a lower fatty acid,
   ii) a nucleic acid-related substance.

Preferably the core is >75% coated, more preferably substantially wholly coated or completely coated. According to the present invention, the biologically active substance may be any type of nutrient preparation, feed, medicine, etc., or a mixture thereof. For example, one or a mixture of two or more substances selected from the group consisting of amino acids and their derivatives, hydroxy homologous compounds of amino acids, proteins, carbohydrates, vitamins, veterinary medicines etc., may be used.

More specifically, amino acids such as lysine, methionine, tryptophan and threonine; amino acid derivatives such as N-acylamino acids, the calcium salt of N-hydroxymethylmethionine and lysine hydrochloride; hydroxy homologous compounds of amino acids such as 2-hydroxy-4-methylmercaptobutyric acid and salts thereof; natural nutrient powders such as grain powder, feather powder and fish powder; proteins such as casein, corn protein and potato protein; carbohydrates such as starch, cane sugar, sucrose and glucose; vitamins such as vitamin A, vitamin A acetate, vitamin A palmitate, vitamins B, thiamine, thiamine hydrochloride, riboflavin, nicotinic acid, nicotinic acid amide, calcium pantothenate, choline pantothenate, pyridoxine hydrochloride, choline chloride, cyanocobalamine, biotin, folic acid, P-aminobenzoic acid, vitamin D2, vitamin D3, vitamin E and substances having similar functions; antibiotics such as tetracycline antibiotics, amino glycoside antibiotics, macrolide antibiotics, and polyether antibiotics; insecticides such as negfon; vermicides such as piperazine; and hormones such as estrogen, stilbestrol, hexestrol, tyroprotein and goitrogen may be used as the invention biologically active substance either alone or in any combination thereof.

There is no particular restriction on the method for the preparation of the core containing the biologically active substance, and granules, preferably granules close to spherical in shape, may be prepared by any commonly used granulating method. For example, extrusion granulation, fluidized granulation, stirring granulation, etc. may be used adding, if necessary, a binder, a filler, etc.

Binders which may be used in the core include cellulose derivatives such as hydroxypropylcellulose, methylcellulose, sodium carboxymethylcellulose, vinyl derivatives such as polyvinyl alcohol, polyvinylpyrrolidone, or gum Arabic, guaiac gum, sodium polyacrylate, etc. Useful fillers include starch, protein, crystalline cellulose, or the like.

The coating composition used to coat the core containing the above mentioned biologically active substance(s) contains at least one substance selected from the group consisting of linear or branched, saturated or mono- or poly-unsaturated aliphatic monocarboxylic acids of 12-22 carbon atoms or salts thereof, hardened vegetable fats and oils, hardened animal fats and oils, and wax, and at least one substance selected from lower fatty acids and nucleic acid-related substances. Also, other known disintegrating agents, for example, inorganic substances which are stable in neutral pH but which become soluble in acidic pH may be added. Chitosan, emulsifiers, e.g., lecithin, etc., may also be included.

The aliphatic monocarboxylic acid of 12-22 carbon atoms of the invention include myristic acid, palmitic acid, stearic acid, oleic acid, linoleic acid, behenic acid, etc., or salts thereof. The hardened vegetable oil may be hardened palm oil, hardened soybean oil, hardened rapeseed oil, hardened castor oil, etc.; the hardened animal oil may be hardened beef tallow, hardened pig oil, etc.; the wax may be carnauba wax, bees wax natural wax, synthetic wax and paraffin wax, etc. The hardened vegetable fats of the invention include hardened sunflower oil, hardened sesame oil, hardened corn oil, etc. The hardened animal fats of the invention include hardened fish oil, hardened whale oil, etc.

The lower fatty acid of the invention includes acids such as undecylic acid, capric acid, caprylic acid, caproic acid, etc., or a mixture thereof. Any $C_1$-$C_{11}$ acid can be used, with $C_5$, $C_6$, $C_7$, $C_8$, $C_9$, $C_{10}$ and $C_{11}$ acids being preferred. Mixtures may be used. The nucleic acid-related substances of the invention include RNA, inosine, guanine, adenosine, etc. or a mixture thereof. In addition, when using all of the above substances, there is no restriction on their purity. However, it is preferred that they not contain known toxic materials.

The coating composition according to the present invention comprises the lower fatty acid and/or nucleic acid-related substance in a proportion of 1-20%, preferably 2-15% by weight, more preferably 3-10% by weight based on the entire coating composition. If the content of these substances in the coating composition exceeds 20%, then the strength of the coating layer is reduced, thus reducing the degree of protection in the rumen. Further, if the proportion by weight is not at least 1% by weight the degree of release of biologically active substance(s) in the abomasum and subsequent digestive tract is reduced.

The material described in a) above is preferably present in said coating composition in 50 to 99% by weight, more preferably 85 to 98% by weight based on the entire coating composition.

The feed additive composition for ruminants according to the present invention is characterized in that a core which contains any biologically active substance(s) is coated with the above mentioned coating composition. There is no particular restriction on the amount of the coating composition used, but a smaller amount is preferable since the content of the biologically active substance may be increased thereby; however, it is necessary that the amount be able to sufficiently protect the biologically active substance in the rumen, and normally the coating is used at 10-200 parts by weight, preferably 15-150 parts by weight, to 100 parts by weight of core containing the biologically active substance.

Furthermore, the feed additive composition for ruminants according to the present invention preferably has its specific gravity adjusted within the range of 1.0-1.5 to speed its passage through the rumen. In cases where the specific gravity cannot be adjusted within this range due to the specific coating and/or biologically active substance used, a specific gravity adjusting agent may be included in the coating composition and/or in the core which contains the biologically active substance, if desired. Specific gravity adjusting agents which may be used include calcium carbonate, calcium phosphate, kaolin, talc, or the like.

There is no particular restriction regarding the method of coating. Any common coating method, for example, fluidized-bed coating, pan coating, melt coating, etc., may be used.

A more detailed description will now be provided regarding the present invention with reference to both Examples and Comparisons, but the scope of the present invention is not limited to these Examples.

EXAMPLES

The degree of usefulness of the invention feed additives was evaluated according to the following methods.

Stability in the rumen

Of a prepared sample, about 2 g was placed into a 200 ml Erlenmeyer flask, 100 ml of a McDougall buffer solution * corresponding to rumen juice was poured therein, and the flask was shaken at a temperature of 39° C. for 24 hours. After completion of the shaking, the degree of release of the biologically active substance was analyzed to calculate the stability in the rumen. In cases where the biologically active substance was an amino acid, the amount thereof released was analyzed by liquid chromatography. * McDougall buffer solution: A buffer solution prepared by dissolving the following reagents in 1000 ml of water.
Sodium bicarbonate: 7.43 g
Disodium phosphate 12H₂O: 7.00 g
Sodium chloride: 0.34 g
Potassium chloride: 0.43 g
Magnesium chloride: 6H₂O: 0.10 g
Calcium chloride: 0.05 g Dissolving property in the abomasum After the stability test, the shaken sample was recovered and the adhered solution was washed off, after which it was placed into a 200 ml Erlenmeyer flask, 40 ml of a Clark-Lubs buffer solution* corresponding to the abomasum juice was poured therein, and the flask was shaken at a temperature of 39° C. for 1 hour. After completion of the shaking, the degree of release of the biologically active substance was analyzed.

* Clark-Lubs buffer solution: A buffer solution prepared by dissolving the following reagents in 1000 ml of water.
Potassium chloride: 3.73 g
Hydrochloric acid: 2.1 ml Dissolving property in the small intestine After the dissolving property inside the abomasum was tested the shaken sample was recovered and placed into a 200 ml Erlenmeyer flask, 100 ml of a buffer solution corresponding to the small intestinal juice (pH 5.5–8.5) was poured therein, and the flask was shaken at a temperature of 39° C. for 7 hours. After completion of the shaking, the degree of release of the biologically active substance was analyzed, and the degree of release in the above mentioned abomasum solution was added to the degree of release in the small intestinal solution to calculate the degree of release in the abomasum and subsequent digestive tract (hereunder referred to as "digestive tract release rate").

Preparation of Core (A) containing L-lysine hydrochloride

A 325 g portion of L-lysine hydrochloride, 172.5 g of talc, 2.5 g of sodium carboxymethylcellulose and 135 g of water were charged into a kneader and kneaded, after which an extruder having a screen with an opening size of 1.5 mm was used to obtain cylindrically-shaped granules.

The obtained granules were formed into granules approaching a spherical shape using a spherical granule producing machine (Marumerizer, Fuji Paudal Co., Ltd). The resulting spherical granules were subjected to fluidized drying to obtain cores containing L-lysine hydrochloride.

Preparation of Core (B) containing D,L-methionine

A 375 g portion of D,L-methionine, 120 g of talc, 5 g of sodium carboxymethylcellulose and 150 g of water were charged into a kneader and kneaded, after which an extruder having a screen with an opening size of 1.5 mm was used to obtain cylindrically-shaped granules. The obtained granules were formed into granules approaching a spherical shape using a spherical granule producing machine (Marumerizer, Fuji Paudal Co., Ltd.). The resulting spherical granules were subjected to fluidized drying to obtain cores containing D,L-methionine.

Example 1

To 95 parts by weight of melted hardened beef tallow (m.p. 61° C.) was added 5 parts by weight of capric acid (carbon number 10), and this mixed coating composition was coated onto Core (A) at a proportion of 43 parts by weight to 100 parts by weight of the core (coating ratio 30%). The coating was effected using a fluidized-bed coater (New Marumelizer, Fuji Paudal Co. Ltd.). The rumen stomach release rate and the digestive tract release rate for this feed additive composition for ruminant animals was determined according to the above mentioned evaluation test, and the results are shown in Table 1.

TABLE 1

| Example | | 1 | 2 | 3 | 4 | 5 | 6 | 7 | 8 |
| --- | --- | --- | --- | --- | --- | --- | --- | --- | --- |
| Core | | A | A | A | A | A | A | B | B |
| Parts by weight (core) | | 100 | 100 | 100 | 100 | 100 | 100 | 100 | 100 |
| Parts by weight (core layer) | | 43 | 67 | 43 | 43 | 43 | 43 | 33 | 33 |
| Coating layer composition (%) | Hardened beef tallow | 95 | 95 | 90 | 97 | 95 | 90 | 95 | 90 |
| | Capric acid | 5 | 5 | 10 | — | — | — | 5 | |
| | Caprylic acid | — | — | — | 3 | 5 | 10 | — | 10 |
| Release rate (%) | Rumen | 7 | 3 | 14 | 5 | 8 | 18 | 6 | 11 |
| | Digestive tract (abomasum + | 55 | 61 | 58 | 48 | 30 | 59 | 55 | 54 |

TABLE 1-continued

| Example | 1 | 2 | 3 | 4 | 5 | 6 | 7 | 8 |
|---|---|---|---|---|---|---|---|---|
| small intestine) | | | | | | | | |

Examples 2–8

Feed additive compositions for ruminant animals having the cores and coating compositions in the amounts shown in Table 1 were prepared in the same manner as in Example 1, and the results of the evaluation tests are shown in Table 1.

Example 9

To 95 parts by weight of melted hardened beef tallow (m.p. 61° C.) was added 5 parts by weight of RNA (trade name "Sanyo Nucleic Acid" product of Sanyo Kokusaku Pulp, Inc.), and this mixed coating composition was coated onto Core (A) at a proportion of 43 parts by weight to 100 parts by weight of the core (coating ratio 30%). The coating was effected using a fluidized-bed coater (New Marumelizer, Fuji Paudal Co. Ltd.). The rumen release rate and the digestive tract release rate for this feed additive composition for ruminant animals was determined according to the above mentioned evaluation tests and the results are shown in Table 2.

TABLE 2

| Example | | 9 | 10 | 11 | 12 | 13 | 14 | 15 | 16 |
|---|---|---|---|---|---|---|---|---|---|
| Core | | A | A | A | A | A | A | B | B |
| Parts by weight (core) | | 100 | 100 | 100 | 100 | 100 | 100 | 100 | 100 |
| Parts by weight (coating layer) | | 43 | 43 | 43 | 25 | 25 | 43 | 33 | 33 |
| Coating layer composition (%) | Hardened beef tallow | 95 | 94 | 95 | 98 | 90 | 88 | 95 | 93 |
| | RNA | 5 | 4 | — | 2 | — | 2 | 5 | 2 |
| | Inosine | — | — | 5 | — | — | — | — | — |
| | Guanine | — | — | — | — | 10 | — | — | — |
| | Capric acid | — | — | — | — | — | 5 | — | — |
| | Lecithin | — | 2 | — | — | — | 5 | — | 5 |
| Release rate (%) | Rumen | 10 | 10 | 11 | 20 | 25 | 8 | 8 | 24 |
| | Digestive tract (abomasum + small intestine) | 40 | 39 | 35 | 48 | 48 | 47 | 46 | 61 |

Examples 10–16

Feed additive compositions for ruminant animals having the cores and coating compositions in the amounts shown in Table 2 were prepared in the same manner as in Example 9, and the results of the evaluation tests are shown in Table 2.

Comparisons 1–8

The cores and coating compositions in amounts shown in Table 3 were combined in the same manner as in Example 1 to prepare coated granules for comparison. The results of the evaluation test are shown in Table 3.

TABLE 3

| Comparison | | 1 | 2 | 3 | 4 | 5 | 6 | 7 | 8 |
|---|---|---|---|---|---|---|---|---|---|
| Core | | A | A | A | A | A | A | B | B |
| Parts by weight (core) | | 100 | 100 | 100 | 100 | 100 | 100 | 100 | 100 |
| Parts by weight (coating layer) | | 43 | 43 | 43 | 43 | 43 | 25 | 33 | 33 |
| Coating layer composition (%) | Hardened beef tallow | 100 | 70 | 99.5 | 90 | 95 | 95 | 95 | 90 |
| | Capric acid | — | 30 | — | — | — | — | — | — |
| | Caprylic acid | — | — | 0.5 | — | — | — | — | — |
| | Stearic acid | — | — | — | 10 | — | — | — | 10 |
| | Oleic acid | — | — | — | — | 5 | 5 | — | — |
| | Palmitic acid | — | — | — | — | — | — | 5 | — |
| Release rate (%) | Rumen | 2 | 87 | 3 | 5 | 4 | 93 | 3 | 5 |
| | Digestive tract (abomasum + small | 1 | 10 | 5 | 8 | 13 | 3 | 7 | 10 |

TABLE 3-continued

| Comparison | 1 | 2 | 3 | 4 | 5 | 6 | 7 | 8 |
|---|---|---|---|---|---|---|---|---|
| intestine | | | | | | | | |

Comparisons 9–12

The cores and coating compositions in amounts shown in Table 4 were combined in the same manner as in Example 9 to prepare coated granules for comparison. The results of the evaluation test are shown in Table 4.

TABLE 4

| Comparison | | 9 | 10 | 11 | 12 |
|---|---|---|---|---|---|
| Core | | A | A | A | B |
| Parts by weight (core) | | 100 | 100 | 100 | 100 |
| Parts by weight (coating layer) | | 43 | 43 | 43 | 43 |
| Coating layer composition (%) | Hardened beef tallow | 100 | 70 | 98 | 100 |
| | RNA | — | 30 | — | — |
| | Inosine | — | — | — | — |
| | Lecithin | — | — | 2 | — |
| Release rate (%) | Rumen | 1 | 82 | 1 | 3 |
| | Digestive tract (abomasum + small intestine | 3 | 10 | 6 | 2 |

From the above results, it may be seen that the feed additive compositions according to the present invention show excellent effects regarding protection in the rumen and release in the abomasum and subsequent digestive tract in comparison to compositions similar to those of the invention.

Accordingly, and as explained above, a feed additive composition for ruminants has been provided which combines both excellent stability in the rumen and excellent release in the abomasum and subsequent digestive tract. These compositions are provided by coating a core which contains a biologically active substance with a coating composition which contains at least one substance selected from the group consisting of one or more substances selected from lower fatty acids and/or nucleic acid-related substances and at least one or more substances selected from linear or branched saturated or unsaturated aliphatic monocarboxylic acids of 12–22 carbon atoms or salts thereof, hardened vegetable fats and oils, hardened animal fats and oils, and wax. These feed additives containing biologically active substances are capable of being efficiently absorbed by ruminants, and therefore are of major significance from an industrial point of view.

WHAT IS CLAIMED AS NEW AND DESIRED TO BE SECURED BY LETTERS PATENT IN THE UNITED STATES IS:

1. A feed additive composition comprising a core and a coating on said core, said core comprising a biologically active substance, said coating comprising components a) and b) below:
   a) at least one substance selected from the group consisting of hardened vegetable fats and oils and hardened animal fats and oils;
   b) from 1–20% by weight, based on the entire weight of the coating, of at least one of substances i) and ii) below:
      i) one or more linear of branched saturated or unsaturated aliphatic monocarboxylic acids having 11 carbon atoms or less and selected from the group consisting of capric acid and caprylic acid
      ii) one or more substances selected from the group consisting of RNA, inosine, guanine and salts thereof.

2. A feed additive composition according to claim 1, wherein said coating comprises hardened beef tallow and at least one of capric acid and caprylic acid.

3. A feed additive composition according to claim 1, wherein said coating comprises hardended beef tallow and at least one of RNA, inosine, guanine and capric acid.

4. A feed additive composition according to claim 1, wherein said biologically active substance is one or a mixture of two or more substances selected from the group consisting of amino acids, proteins, carbohydrates, vitamins and veterinary medicines.

5. A feed additive composition according to claim 1, wherein component a) is at least one substance selected from the group consisting of hardened beef tallow, hardened sunflower oil, hardened sesame oil, hardened corn oil, hardened fish oil and hardened whale oil.

6. A feed additive composition according to claim 1, wherein said biologically active substance is selected from the group consisting of L-lysine hydrochloride and D,L-methionine.

7. A feed additive composition according to claim 2, wherein said biologically active substance is selected from the group consisting of L-lysine hydrochloride and D,L-methionine.

8. A feed additive composition according to claim 3, wherein said biologically active substance is selected from the group consisting of L-lysine hydrochloride and D,L-methionine.

9. A feed additive composition according to claim 5, wherein said biologically active substance is selected from the group consisting of L-lysine hydrochloride and D,L-methionine.

10. A feed additive composition according to claim 1, wherein component a) is present in an amount of from 50 to 99% by weight based on the entire weight of the coating composition.

11. A feed additive composition according to claim 2, wherein component a) is present in an amount of from 50 to 99% by weight based on the entire weight of the coating composition.

12. A feed additive composition according to claim 3, wherein component a) is present in an amount of from 50 to 99% by weight based on the entire weight of the coating composition.

13. A feed additive composition according to claim 5, wherein component a) is present in an amount of from 50 to 99% by weight based on the entire weight of the coating composition.

14. A feed additive composition according to claim 6, wherein component a) is present in an amount of from 50 to 99% by weight based on the entire weight of the coating composition.

* * * * *